(12) United States Patent
Lepak et al.

(10) Patent No.: US 6,214,026 B1
(45) Date of Patent: Apr. 10, 2001

(54) DELIVERY SYSTEM FOR A VASCULAR DEVICE WITH ARTICULATION REGION

(75) Inventors: Jonah Lepak, Santa Cruz; Farhad Khosravi, San Mateo; Amr Salahieh, Campbell, all of CA (US)

(73) Assignee: Incept LLC, San Mateo, CA (US)

( * ) Notice: Subject to any disclaimer, the term of this patent is extended or adjusted under 35 U.S.C. 154(b) by 0 days.

(21) Appl. No.: 09/470,682

(22) Filed: Dec. 23, 1999

Related U.S. Application Data

(63) Continuation-in-part of application No. 09/364,064, filed on Jul. 30, 1999.

(51) Int. Cl.[7] .................................................. A61B 17/22
(52) U.S. Cl. ........................................... 606/200; 604/104
(58) Field of Search ................................. 606/200, 191, 606/108, 1; 604/104

(56) References Cited

U.S. PATENT DOCUMENTS

| | | | |
|---|---|---|---|
| 3,592,186 | 7/1971 | Oster | 128/2 R |
| 3,683,904 | 8/1972 | Forster | 128/127 |
| 3,952,747 | 4/1976 | Kimmell, Jr. | 128/303 R |
| 3,996,938 | 12/1976 | Clark, III | 128/348 |
| 4,046,150 | 9/1977 | Schwartz et al. | 128/328 |
| 4,662,885 | 5/1987 | DiPisa, Jr. | 623/12 |
| 4,705,517 | 11/1987 | DiPisa, Jr. | 623/12 |
| 4,706,671 | 11/1987 | Weinrib | 128/348 |
| 4,723,549 | 2/1988 | Wholey et al. | 128/344 |
| 4,790,812 | 12/1988 | Hawkins, Jr. et al. | 604/22 |
| 4,794,928 | 1/1989 | Kletschka | 128/344 |
| 4,807,626 | 2/1989 | McGirr | 128/328 |
| 4,873,978 | 10/1989 | Ginsburg | 128/345 |
| 4,921,478 | 5/1990 | Solano et al. | 604/53 |
| 4,921,484 | 5/1990 | Hillstead | 604/104 |
| 4,926,858 | 5/1990 | Gifford et al. | 606/159 |
| 4,969,891 | 11/1990 | Gewertz | 606/200 |
| 4,998,539 | 3/1991 | Delsanti | 128/898 |
| 5,002,560 | 3/1991 | Machold et al. | 606/198 |

(List continued on next page.)

FOREIGN PATENT DOCUMENTS

| | | | |
|---|---|---|---|
| 0 427 429 A1 | 5/1991 | (EP) | A61M/25/10 |
| 0 655 228 A1 | 11/1994 | (EP) | A61F/2/02 |
| 0 737 450 A1 | 10/1996 | (EP) | A61F/2/01 |
| 0 743 046 A1 | 11/1996 | (EP) | A61F/2/01 |
| 0 759 287 A1 | 2/1997 | (EP) | A61F/2/01 |
| 0 771 549 A2 | 5/1997 | (EP) | A61F/2/01 |
| 0 784 988 A1 | 7/1997 | (EP) | A61M/5/165 |
| 0 852 132 A1 | 7/1998 | (EP) | A61F/2/01 |
| 2 020 557 | 11/1979 | (GB) | A61B/17/50 |
| WO 94/14389 | 7/1994 | (WO) | A61F/2/02 |
| WO 96/01591 | 1/1996 | (WO) | A61B/17/22 |
| WO 97/27808 | 8/1997 | (WO) | A61B/17/22 |

(List continued on next page.)

OTHER PUBLICATIONS

Wholey, Mark H. et al., "PTA and Stents in the Treatment of Extracranial Circulation," *The Journal of Invasive Cardiology*: vol. 8/Supplement E, Health Management Publications, Inc., 1996, pp. 25E–30E.

Primary Examiner—Gary Jackson
(74) Attorney, Agent, or Firm—Fish & Neave; Nicola A. Pisano; Kenneth J. Michlitsch

(57) ABSTRACT

Apparatus and methods are provided for use in deploying and retrieving a vascular device suited for filtering emboli from a vessel and performing thrombectomy and embolectomy. The vascular device comprises a support hoop having an articulation region connected near a distal end of a guide wire, and a blood permeable sac affixed to the support hoop so that the support hoop forms a mouth of the blood permeable sac. A specialized delivery system allows precise control over deployment and retrieval of the vascular device, and the introduction or withdrawal of fluids from an operative site.

20 Claims, 3 Drawing Sheets

U.S. PATENT DOCUMENTS

| | | | |
|---|---|---|---|
| 5,071,407 | 12/1991 | Termin et al. | 604/104 |
| 5,102,415 | 4/1992 | Guenther et al. | 606/159 |
| 5,108,419 | 4/1992 | Reger et al. | 606/200 |
| 5,133,733 | 7/1992 | Rasmussen et al. | 606/200 |
| 5,171,233 | 12/1992 | Amplatz et al. | 604/281 |
| 5,329,942 | 7/1994 | Gunther et al. | 128/898 |
| 5,354,310 | 10/1994 | Garnic et al. | 606/198 |
| 5,370,657 | 12/1994 | Irie | 606/200 |
| 5,383,887 | 1/1995 | Nadal | 606/200 |
| 5,415,630 | 5/1995 | Gory et al. | 604/53 |
| 5,421,832 | 6/1995 | Lefebvre | 604/53 |
| 5,456,667 | 10/1995 | Ham et al. | 604/107 |
| 5,476,104 | 12/1995 | Sheahon | 128/757 |
| 5,549,626 | 8/1996 | Miller et al. | 606/200 |
| 5,658,296 | 8/1997 | Bates et al. | 606/127 |
| 5,662,671 | 9/1997 | Barbut et al. | 606/170 |
| 5,669,933 | 9/1997 | Simon et al. | 600/200 |
| 5,695,519 | 12/1997 | Summers et al. | 606/200 |
| 5,746,758 | 5/1998 | Nordgren et al. | 606/159 |
| 5,769,816 | 6/1998 | Barbut et al. | 604/96 |
| 5,779,716 | 7/1998 | Cano et al. | 606/114 |
| 5,792,300 | 8/1998 | Inderbitzen et al. | 156/244.13 |
| 5,795,322 | 8/1998 | Boudewijn | 604/22 |
| 5,797,952 | 8/1998 | Klein | 606/198 |
| 5,800,457 | 9/1998 | Gelbfish | 606/200 |
| 5,800,525 | 9/1998 | Bachinski et al. | 623/1 |
| 5,814,064 | 9/1998 | Daniel et al. | 606/200 |
| 5,817,102 | 10/1998 | Johnson et al. | 606/108 |
| 5,827,324 | 10/1998 | Cassell et al. | 606/200 |
| 5,833,644 | 11/1998 | Zadno-Azizi et al. | 604/52 |
| 5,833,650 | 11/1998 | Imran | 604/53 |
| 5,846,260 | 12/1998 | Maahs | 606/200 |
| 5,876,367 | 3/1999 | Kaganov et al. | 604/8 |
| 5,893,867 | 4/1999 | Bagaoisan et al. | 606/198 |
| 5,895,399 | 4/1999 | Barbut et al. | 606/159 |
| 5,954,745 | 9/1999 | Gertler et al. | 606/200 |
| 5,011,488 | 4/1991 | Ginsburg | 606/159 |
| 5,053,008 | 10/1991 | Bajaj | 604/104 |

FOREIGN PATENT DOCUMENTS

| | | | |
|---|---|---|---|
| WO 97/42879 | 11/1997 | (WO) | A61B/17/00 |
| WO 98/23322 | 6/1998 | (WO) | A61M/29/00 |
| WO 98/33443 | 8/1998 | (WO) | A61B/17/22 |
| WO 98/34673 | 8/1998 | (WO) | A61M/31/00 |
| WO 98/36786 | 8/1998 | (WO) | A61M/5/32 |
| WO 98/38920 | 9/1998 | (WO) | A61B/17/22 |
| WO 98/38929 | 9/1998 | (WO) | A61B/17/00 |
| WO 98/39053 | 9/1998 | (WO) | A61M/29/00 |
| WO 98/46297 | 10/1998 | (WO) | A61M/29/00 |
| WO 98/47447 | 10/1998 | (WO) | A61F/2/06 |
| WO 98/50103 | 11/1998 | (WO) | A61M/29/00 |
| WO 98/51237 | 11/1998 | (WO) | A61F/2/01 |
| WO 98/55175 | 12/1998 | (WO) | A61M/29/00 |
| WO 99/09895 | 3/1999 | (WO) | A61B/17/12 |
| WO 99/23976 | 5/1999 | (WO) | A61F/2/01 |

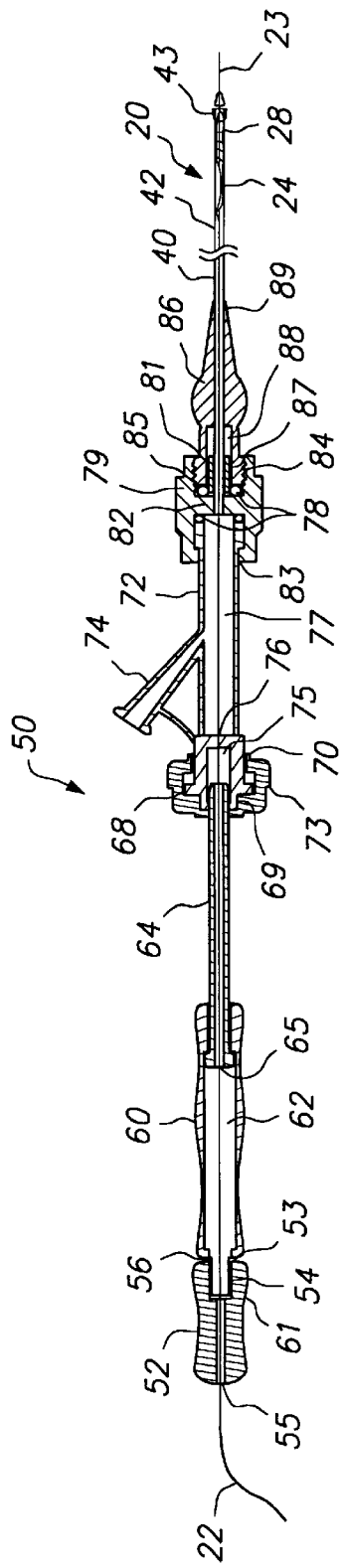
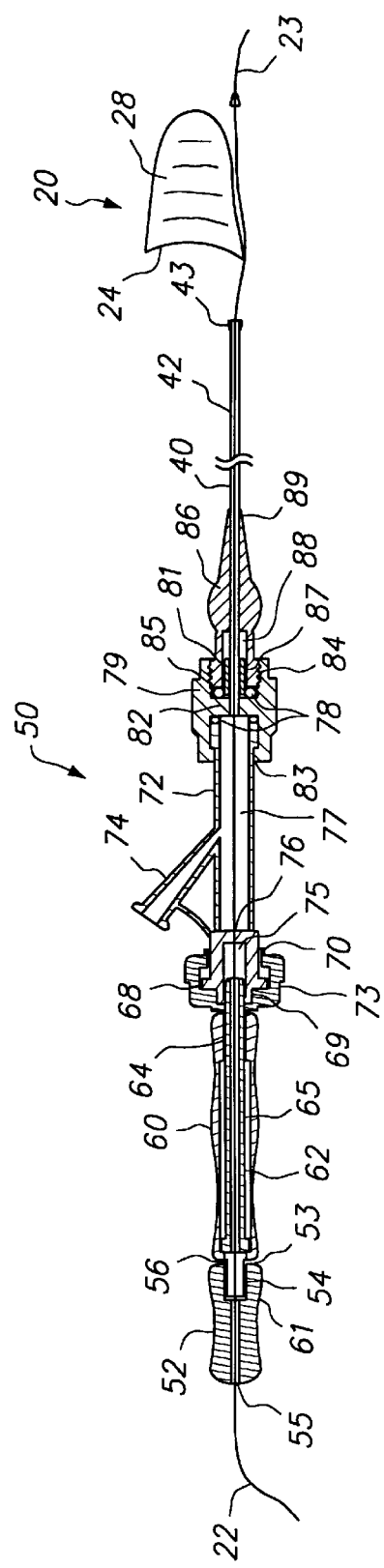
FIG. 5A
FIG. 5B

DELIVERY SYSTEM FOR A VASCULAR DEVICE WITH ARTICULATION REGION

REFERENCE TO RELATED APPLICATIONS

This application is a continuation-in-part of U.S. patent application Ser. No. 09/364,064 filed Jul. 30, 1999, now pending.

FIELD OF THE INVENTION

The present invention relates to apparatus and methods for filtering or removing matter from within a vascular system. More particularly, the present invention provides a delivery system for a low profile, self-expanding vascular device useful for capturing emboli generated during interventional procedures, and for thrombectomy and embolectomy.

BACKGROUND OF THE INVENTION

Percutaneous interventional procedures to treat occlusive vascular disease, such as angioplasty, atherectomy, and stenting, often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, also involves the introduction of foreign objects into the bloodstream, and also may result in the formation of clots or release of emboli. Such particulate matter, if released into the bloodstream, also may cause infarction or stroke.

Numerous previously known methods and apparatus have been proposed to reduce the risk of embolism. U.S. Pat. No. 5,833,644 to Zadno-Azizi et al., for example, describes the use of balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and any interventional devices, such as an angioplasty balloon or stent delivery system are advanced along the guide wire. The filter is designed to capture emboli generated during treatment of the stenosis while permitting blood to flow through the filter. Similar filter systems are described in Wholey et al. U.S. Pat. No. 4,723,549 and Cassell et al. U.S. Pat. No. 5,827,324.

One disadvantage of radially expandable filter systems such as described in the foregoing patents is the relative complexity of the devices, which typically comprise numerous parts. Connecting more than a minimal number of such parts to a guide wire generally increases delivery complications. The ability of the guide wire to negotiate tortuous anatomy diminishes, and the profile of the device in its delivery configuration increases. Consequently, it may be difficult or impossible to use such devices in small diameter vessels such as are commonly found in the carotid artery and cerebral vasculature. Moreover, such filter devices are generally incapable of preventing material from escaping from the filter during the process of collapsing the filter for removal.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, compared to the radial strut-type filter elements described hereinabove, it too has drawbacks. Chief among these, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly and is expected to result in a delivery profile too large to permit use of the device in critical regions of the body, such as the smaller coronary arteries, carotid arteries, and cerebral vasculature.

In view of the foregoing disadvantages of previously known apparatus and methods, a need still exists for a vascular device with a reliable and multi-functional delivery system, e.g., for use as a vascular filter. It would therefore be desirable to provide a delivery system for a vascular device that overcomes the foregoing disadvantages.

It further would be desirable to provide a delivery system for a vascular device that integrates multiple delivery functions of previously known devices into a single device.

It further would be desirable to provide a delivery system for a vascular device that facilitates positioning of the vascular device in a bifurcated vessel.

It still further would be desirable to provide a delivery system for a vascular device that facilitates the addition or removal of fluids from the operative site.

It further would be desirable to provide a delivery system for a vascular device that provides precise control over the deployment and retrieval of the vascular device.

SUMMARY OF THE INVENTION

In view of the foregoing, it is an object of the present invention to provide a delivery system for a vascular device that overcomes disadvantages associated with previously known vascular filters and thrombectomy/embolectomy systems.

It is also an object of this invention to provide a delivery system for a vascular device that integrates multiple delivery functions of previously known devices into a single device.

It is another object of this invention to provide a delivery system for a vascular device that facilitates positioning of the vascular device in a bifurcated vessel.

It is yet another object of this invention to provide a delivery system for a vascular device that facilitates the addition or removal of fluids from the operative site.

It is further an object of this invention to provide a delivery system for a vascular device that provides precise control over the deployment and retrieval of the vascular device.

These and other objects of the present invention are accomplished by providing a delivery system for a vascular device, suitable for use as a vascular filter or thrombectomy/ embolectomy device. The delivery system integrates the functions of a Touhy Borst, a torquer, and a pusher into a single device, and is configured for use with the vascular device described in commonly assigned, co-pending U.S. patent application Ser. No. 09/364,064 filed Jul. 30, 1999, which is incorporated herein by reference.

In a preferred embodiment, the vascular device comprises a blood permeable sac affixed at its perimeter to a support hoop having an articulation region. The reduced-thickness articulation region enables contraction of the support hoop to very small radii of curvature without increased stiffness and kinking. The hoop is attached in a distal region of an elongated member, such as a guide wire, and supports a proximally-oriented mouth of the sac when the device is deployed in a vessel. The sides of the support hoop fold inwards towards one-another when the vascular device is collapsed into a sheath for removal. This in turn closes the mouth of the sac and reduces the potential for emboli or thrombus to be released from the vascular device during removal.

The delivery system of the present invention facilitates introduction and retrieval of the vascular device. The torqueing function allows the vascular device to navigate tortuous anatomy. For example, the distal end of the guide wire may be rotated to selectively orient the vascular device in a selected branch of a bifurcated vessel. The Touhy-Borst adapter permits liquid to be introduced or withdrawn through the lumen of the vascular device delivery catheter. The wire feature of the delivery system allows deployment and retraction of the vascular device from within the delivery catheter.

Methods of using the delivery means of the present invention in conjunction with the vascular device also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 5A and 5B are side sectional views of a delivery system constructed in accordance with the present invention coupled to the vascular device of FIG. 4A, and show, respectively, the vascular device in the contracted and deployed states.

DETAILED DESCRIPTION OF THE INVENTION

The present invention is directed to a delivery system suitable for use with a vascular filter or thrombectomy/ embolectomy device, such as described in co-pending, commonly assigned U.S. patent application Ser. No. 09/364,064, filed Jul. 30, 1999, incorporated herein by reference. In a preferred embodiment, the vascular device comprises a self-expanding support hoop that is sufficiently thick to radially expand and urge a blood permeable sac into engagement with a vessel wall, but which includes an articulation region that eliminates kinking. More specifically, the vascular device includes a reduced thickness articulation region and a pre-formed curved profile that avoids some of the drawbacks of previously known systems, while providing a high degree of efficacy in capturing emboli or thrombus, and ease of deployment and retrieval. In accordance with the principles of the present invention, a delivery system is provided that facilitates deployment and retrieval of the vascular device, and comprises an integrated device that performs the functions of a torquer, a Touhy Borst adapter, and a pusher.

Figure 1A:
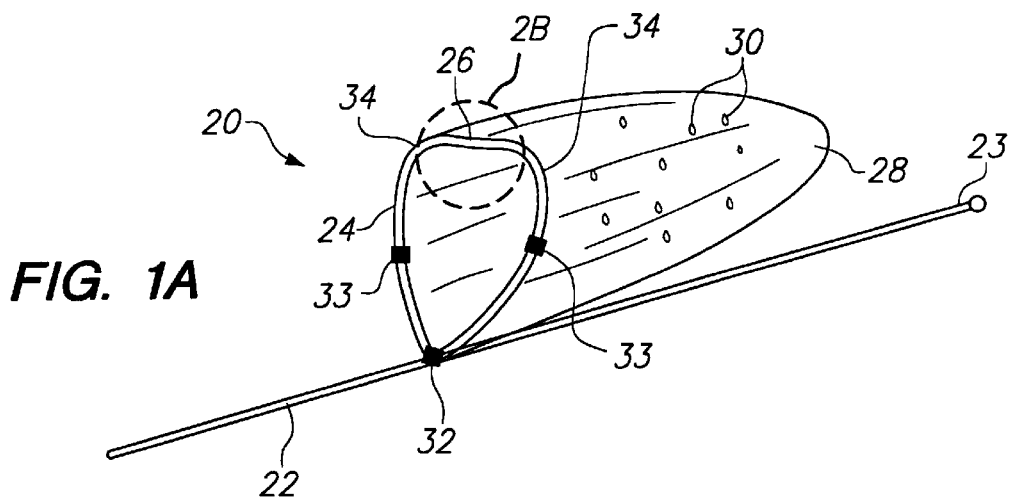
FIGS. 1A and 1B are, respectively, a perspective view of a vascular device configured for use with the delivery system of the present invention in a deployed state, and a detailed view of the articulation region of the device of FIG. 1A.
Figure 1B:
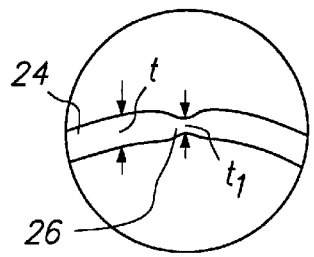

Referring now to FIGS. 1A and 1B, vascular device 20, illustratively an embolic filter, comprises guide wire 22, support hoop 24 having articulation region 26, and blood permeable sac 28 affixed to support hoop 24. Sac 28 is coupled to support hoop 24 so that the support hoop forms an opening for the sac. Support hoop 24 preferably is connected to guide wire 22 near distal end 23 of the guide wire.

Sac 28 preferably is constructed of a thin, flexible, biocompatible material, such as polyethylene, polypropylene, polyurethane, polyester, polyethylene tetraphlalate, nylon or polytetrafluoroethylene, or combinations thereof, and includes openings or pores 30 that permit blood cells to pass through the sac substantially unhindered, while capturing any larger emboli that may be released during a procedure such as angioplasty or stent placement.

Support hoop 24 comprises a hoop having a circular or rectangular cross-section, and preferably is formed of a super-elastic material, such as a nickel-titanium alloy ("nitinol"). During deployment and retrieval of vascular device 20, support hoop 24 folds in half and collapses to fit within a small diameter delivery sheath. When vascular device 20 is in a deployed state, as depicted in FIG. 2A, support hoop 24 resumes its pre-formed shape.

Support hoop 24 includes reduced-thickness articulation region 26 disposed opposite to point 32 at which support hoop 24 is affixed to guide wire 22. More specifically, support hoop 24 is pre-formed to form a structure having articulation region 26 interposed between curved regions 34. As depicted in FIG. 2B, articulation region 26 includes a region having reduced thickness $t_1$ compared to thickness t of the remainder of support hoop 24. Articulation region 26 and curved regions 34 enable support hoop 24 to fold with a pre-determined shape when vascular device 20 is collapsed to a contracted state for delivery or retrieval. Support hoop 24 also may include radiopaque features, such as gold or platinum bands 33, spaced at intervals around the circumference of support hoop 24.

In a preferred embodiment, vascular device 20 fits within a delivery sheath having an inner diameter of 0.033", and more preferably, may be used with a delivery sheath having an inner diameter as small as 0.026". The deployed diameter of support hoop 24 preferably is approximately 7 mm, while guide wire 22 preferably has a diameter of 0.014", and tapers at its distal end. The distal end of guide wire 22 also may be tipped with a spring section, or coil tip (not shown).

Figure 2:
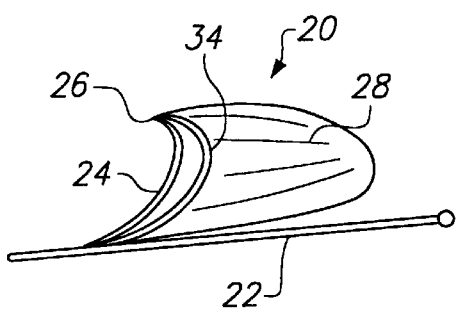
FIG. 2 is a perspective view of the vascular device in a folded configuration, prior to removal.
Figure 3:
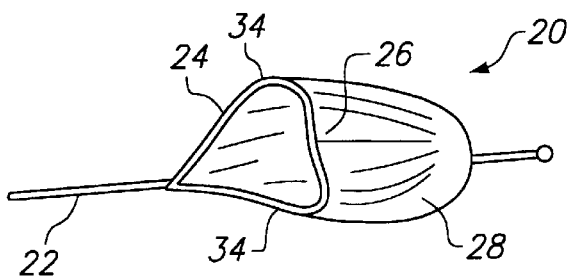
FIG. 3 is a plan view of the vascular device of FIG. 1A.

With respect to FIGS. 2 and 3, additional features of vascular device 20 are described. FIG. 2 depicts vascular device 20 of FIG. 1A in a contracted state, while FIG. 3 illustrates a directional change in support hoop 24 preferably caused by the presence of curved regions 34. In the embodiment depicted in FIG. 3, curved regions 34 illustratively are configured to orient articulation region 26 in a direction parallel to the axis of guide wire 22.

Advantageously, use of articulation region 26 and the curved profile of support hoop 24 introduced by curved regions 34 cause support hoop 24 to fold in half during retrieval. As shown in FIG. 2, support hoop 24 folds in half, effectively closing the mouth of blood permeable sac 28 and preventing the escape of collected emboli or thrombus. Alternatively, articulation region 26 may comprise a gap in support hoop 24, with blood permeable sac 28 affixed to the support hoop to bridge the gap, as described in concurrently filed U.S. patent application Ser. No. 09/470,857, now U.S. Pat. No. 6,129,739.

Figure 4A:
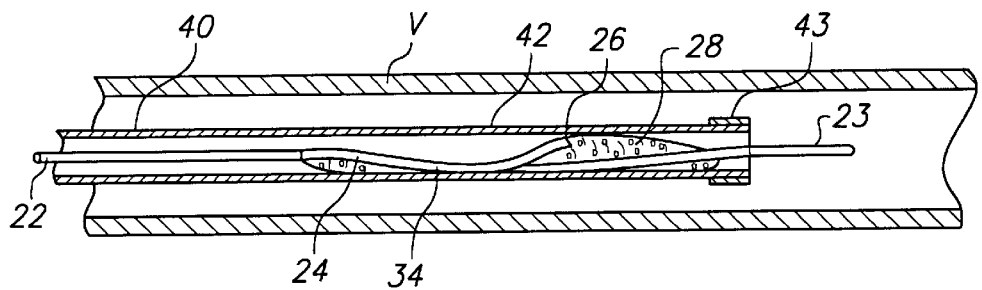
FIGS. 4A–4D are side sectional views depicting a method of deploying, using and retrieving the vascular device.

Referring now to FIGS. 4A–4D, methods of using the vascular device as a vascular filter are described. In FIG. 4A, guide wire 22 is manipulated into position within vessel V using well-known percutaneous techniques. Vascular device 20 of FIG. 1A is disposed in its contracted delivery state within distal end 42 of delivery sheath 40 and delivery sheath 40 is advanced through the vessel using distal 23 of guide wire 22. Articulation region 26 and curved regions 34 of support hoop 24 enable the sides of the support hoop to fold together and become elongated when drawn within delivery sheath 40.

Figure 4B:
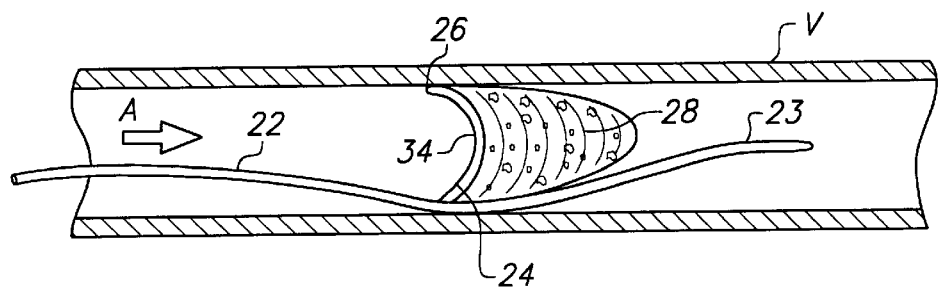
Figure 4C:
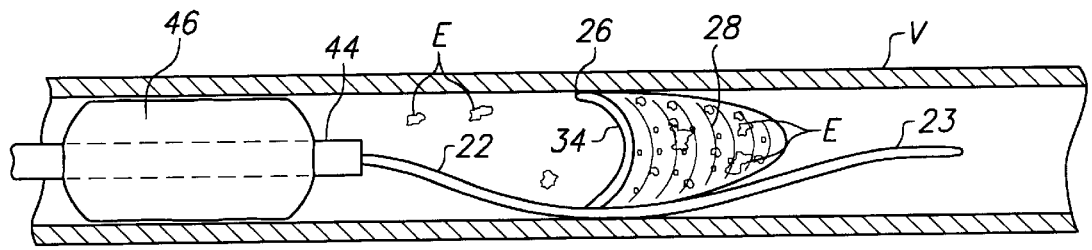
Figure 4D:
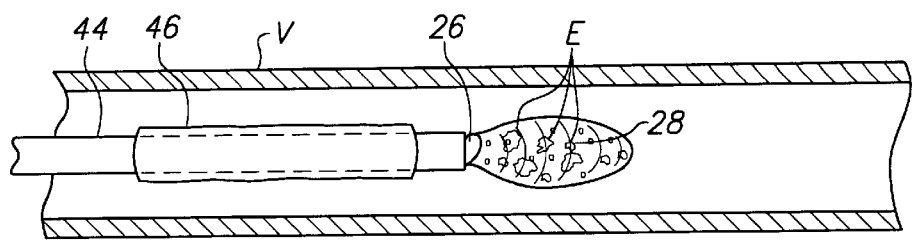

With respect to FIG. 4D, once delivery sheath 40 is disposed at a desired location within a patient's vessel V, such as a coronary artery or carotid artery, for example, based on the position of radiopaque band 43 under a fluoroscope, guide wire 22 is held stationary while delivery sheath 40 is retracted proximally. Alternatively, delivery sheath 40 may be held stationary while guide wire 22 is advanced. In either case, when vascular device 20 is no longer confined within delivery sheath 40, support hoop 24 expands so that curved regions 34 seal against the walls of the vessel V. Blood continues to flow unimpeded through vessel V in direction A.

In FIG. 4C, once vascular device 20 is deployed in vessel V, other interventional instruments, such as angioplasty catheters, atherectomy devices, or stent delivery systems, may be advanced along guide wire 22 to position such devices at treatment zones located proximally of vascular device 20. For example, in FIG. 4C, angioplasty balloon catheter 44 has been advanced along guide wire 22 to a position proximal of vascular device 20 to trap emboli E, i.e., pieces of plaque dislodged from the walls of vessel V by balloon 46.

With respect to FIG. 4D, upon completion of the angioplasty procedure using angioplasty balloon catheter 44, guide wire 22 is pulled proximally to cause the sides of support hoop 24 to collapse together to close the mouth of sac 28 (see FIG. 2). Additional proximal retraction of guide wire 22 causes support hoop 24 and sac 28 to enter at least partially within the guide wire lumen of angioplasty catheter 44. As depicted in FIG. 4D, only a portion of support hoop 24, near articulation region 26, and a distal portion of sac 28 extend out of the guide wire lumen of angioplasty catheter 44. Angioplasty catheter 44 then is withdrawn with vascular device 20 and any trapped emboli E.

Alternatively, vascular device 20 may be used in performing thrombectomy/embolectomy. In this case, vascular device is deployed in a vessel at a location distal to a lesion, in the manner depicted in FIGS. 4A and 4B. Once support hoop 24 is deployed into contact with the vessel wall, vascular device 20 may be retracted proximally to scrape along the wall of the vessel, and excise thrombus so that it is captured in sac 28. Delivery sheath 44 may then be re-inserted into the vessel along guide wire 22, and vascular device 20 is retracted and removed from the vessel.

In accordance with the present invention, a delivery system is provided for use with vascular device 20 that facilitates deployment and retrieval of the vascular device. The delivery system integrates the functions of a torquer, a Touhy Borst adapter, and a pusher into a single device.

Referring now to FIGS. 5A and 5B, a delivery system configured for use with the vascular device of FIGS. 1–3 is described. In FIG. 5A, vascular device 20 is in the retracted state, while in FIG. 5B vascular device 20 is in the deployed state. Delivery system 50 comprises proximal screw cap 52, collet 56, handle 60, rod 64, central screw cap 68, lumen flushing section 72, distal hub 79, and nose piece 86.

Proximal screw cap 52 includes bore 53 with female screw thread 54 and guide wire lumen 55. Bore 53 extends proximally from the distal face of cap 52. Guide wire lumen 55 extends from the proximal end of bore 53 to the proximal end of cap 52.

Handle 60 comprises proximal male screw thread 61 configured to engage female screw thread 54 of cap 52, and lumen 62 configured to receive collet 56 in its proximal end and rod 64 in its distal end. Lumen 62 has a reduced diameter at the distal end of handle 60 that captures a step on the proximal end of rod 64. Thus, while collet 56 is removable received within lumen 62, rod 64 may translate and rotate within, but may not be removed from, lumen 62. Guide wire 22 freely passes through collet 56 when screw cap 52 is not securely fastened to handle 60. When cap 52 is securely fastened to handle 60, it causes collet 56 to elastically deform, decreasing the diameter of the lumen extending through the collet, and frictionally locking guide wire 22 into rigid attachment with collet 56. Guide wire 22 is thereby rigidly connected to handle 60.

Rod 64 further comprises guide wire lumen 65 extending therethrough. Rod 64 has its distal end rigidly and permanently affixed to central screw cap 68. Cap 68 comprises female screw thread 69 and lumen 70. Lumen 70 includes a proximal reduced-diameter step that captures rod 64 within the proximal end of cap 68, and a distal portion that receives lumen flushing or fluid port section 72.

Section 72 comprises male screw thread 73, side port 74, bore 75, guide wire lumen 76, and fluid lumen 77. Male screw thread 73 is configured to engage female thread 69 of cap 68. Section 72 includes a flange disposed just distal of thread 73 that is captured within lumen 70 of cap 68. Thus, cap 68 may be tightened onto and loosened from, but not removed from, section 72.

Rod 64 is received within bore 75 of section 72. Guide wire 22 passes between bore 75 and fluid lumen 77 within guide wire lumen 76. Fluid lumen 77 connects side port 74 to the guide wire lumen of delivery sheath 40. O-rings 78 provide a fluid seal at the distal end of lumen 77.

Distal hub 79 connects section 72 to nose piece 86. Hub 79 comprises bore 83, female screw thread 84, and annulus 85 containing tapered projection 81. Bore 83 includes flange 82 that rotatably receives section 72 in its proximal end. Nose piece 86 comprises male screw thread 87, tapered bore 88, and delivery sheath lumen 89. Male screw thread 87 is configured to engage female thread 84 in annulus 85 of hub 79. Tapered bore 88 allows tapered projection 81 of hub 79 to extend within nose piece 86 and permit delivery sheath 40 from delivery sheath lumen 89 to extend therethrough. O-rings 78 are disposed between the hub 79 and nose piece 86 and between hub 79 and section 72.

Delivery system 50 advantageously may be implemented in a variety of ways. For example, the delivery system may be offered with a delivery catheter or sheath pre-attached. In this embodiment, proximal screw cap 52 is loosened, and the proximal end of guide wire 22 may be passed through the delivery catheter or sheath, and delivery system 50, until vascular device 20 is in its retracted state within the delivery catheter or sheath. Insertion of the vascular device into the patient may then proceed. Alternatively, delivery system 50 may be commercially supplied in the configuration shown in FIG. 5A, i.e., pre-loaded with a delivery catheter or sheath, such as sheath 40, already attached and vascular device 20 retracted therein. As another alternative, delivery system 50 may be offered without either a delivery sheath or vascular device attached, or the delivery catheter or sheath may be an interventional instrument, such as an angioplasty, atherectomy, or stent delivery catheter.

Referring now to FIGS. 4A–4D and 5A and 5B, a method of using the delivery system of the present invention in conjunction with a vascular filter is described. With vascular device 20 contracted within distal end 42 of delivery sheath 40 (FIGS. 4A and 5A), delivery sheath 40 is attached to delivery system 50 by loosening proximal screw cap 52 and extending the proximal end of guide wire 22 through delivery system 50, with handle 60 in its proximal-most position (FIG. 5A). Screw cap 52 is then tightened to cause collet 56 to engage guide wire 22 to handle 60.

Delivery sheath 40 then is advanced through a patient's vasculature using well-known percutaneous techniques using distal end 23 of guide wire 22. If a vessel bifurcation is to be crossed during advancement, handle 60 may be rotated to divert the distal end of sheath 40 into the desired branch of the bifurcation. The rotational moment or torque applied to handle 60 is transmitted to guide wire 22 (when screw cap 52 is tightened), which causes distal end 23 to rotate and facilitates positioning of vascular device 20 in the proper side of the bifurcation. As shown in FIG. 4A, advancement continues until delivery sheath 40 is disposed at a desired location within a patient's vessel V, such as a coronary or carotid artery, as determined, for example, by the position of radiopaque band 43 under a fluoroscope.

With the vascular device in position, handle 60, and thus guide wire 22, is held stationary while the section 72 and attached delivery sheath 40 are retracted proximally. Alternatively, handle 60 may be advanced while section 72 and sheath 40 are held stationary. In either case, when vascular device 20 is no longer confined within delivery sheath 40, support hoop 24 expands to seal against the walls of the vessel V, as depicted in FIGS. 4B and 5B. Blood continues to flow unimpeded through vessel V in direction A.

Depending on the medical procedure prescribed in conjunction with the use of vascular device 20, delivery sheath 40 may retrieve vascular device 20 at the conclusion of the procedure, or sheath 40 may be detached from delivery system 50 and removed from the patient. If sheath 40 is detached, guide wire 22 may be removed from delivery system 50 so that other interventional instruments, such as angioplasty catheters, atherectomy devices, or stent delivery systems may be advanced along guide wire 22 to position such devices at treatment zones located proximally of vascular device 20. Guide wire 22 and the interventional catheter then may be passed through and fastened to delivery system 50. For example, as shown in FIG. 4C, angioplasty balloon catheter 44 may be advanced along guide wire 22 to a position proximal of vascular device 20 so that device 20 may trap emboli E, i.e., pieces of plaque dislodged from the walls of vessel V by balloon 46.

Upon completion of the angioplasty procedure using angioplasty balloon catheter 44, handle 60 with attached guide wire 22 is pulled proximally to cause the sides of support hoop 24 to collapse together to close the mouth of sac 28 (FIG. 2). Additional proximal retraction of guide wire 22 causes support hoop 24 and sac 28 to enter at least partially within the guide wire lumen of angioplasty catheter 44. As depicted in FIG. 4D, only a portion of support hoop 24, near articulation region 26, and a distal portion of sac 28 extend out of the guide wire lumen of angioplasty catheter 44. Angioplasty catheter 44 then is withdrawn with vascular device 20 and any trapped emboli E.

It also may be beneficial during a medical procedure to introduce or withdraw fluids from the operative site. For example, it may be beneficial to deliver medicaments, or draw suction to remove blood. The delivery sheath lumen also may require flushing with saline to prevent clotting within the lumen. These and other procedures are made possible by side port 74 of section 72, which, as described hereinabove, is in fluid communication with the lumen of delivery sheath 40.

In addition to applications with vascular filters, delivery system 50 may be used as part of the thrombectomy/embolectomy procedure described herein above, as well as in a variety of other procedures.

Although preferred illustrative embodiments of the present invention have been described, it will be evident to one skilled in the art that various changes and modifications may be made without departing from the invention. It is intended in the appended claims to cover all such changes and modifications that fall within the true spirit and scope of the invention.

What is claimed is:

1. Apparatus for deploying and retrieving a vascular device disposed on an elongated member from within a lumen of a delivery sheath, the apparatus comprising:
   a handle having a collet for selectively grasping and releasing the elongated member;
   and a lumen flushing section coupled to the handle to allow translation and rotation therebetween, the lumen flushing section having a side port in fluid communication with the lumen of the delivery sheath and configured to allow the elongated member to pass therethrough to the handle.

2. The apparatus of claim 1, wherein the vascular device further comprises:
   a support hoop attached to a distal region of the elongated member, the support hoop having an articulation region interposed between curved regions, and a blood permeable sac affixed to the support hoop so that the support hoop forms a mouth of the blood permeable sac.

3. The apparatus of claim 2, wherein the apparatus has a delivery state, wherein the handle is translated longitudinally to a proximal-most position relative to the lumen flushing section, and the support hoop is retracted within the delivery sheath, and a deployed state wherein the handle is translated longitudinally to a distal-most position adjacent the lumen flushing section, wherein the support hoop extends beyond a distal end of the delivery sheath and engages an interior wall of a patient's vessel.

4. The apparatus of claim 3, wherein the support hoop folds at the articulation region when the vascular device is contracted to the delivery state.

5. The apparatus of claim 3, wherein the mouth of the blood permeable sac is closed when the apparatus is in the delivery state.

6. The apparatus of claim 5 wherein opposite sides of the support hoop close towards one another when the apparatus is contracted to its delivery state.

7. The apparatus of claim 1 wherein the elongated member serves as a guide wire.

8. A method of deploying and retrieving a vascular device suitable for trapping emboli or thrombus during a medical procedure, the method comprising:

providing apparatus comprising a vascular device disposed on an elongated member within a lumen of a delivery sheath, a fluid port section coupled to the delivery sheath, and a handle coupled to the fluid port section for relative translation and rotation;

positioning the elongated member through the fluid port section;

engaging the elongated member to the handle so that motion of the handle is transmitted to the elongated member; and advancing the delivery sheath to a desired location within a patient's vessel.

9. The method of claim 8 further comprising:

translating the fluid port section proximally relative to the handle to withdraw the delivery sheath from a distal region of the elongated member;

expanding the vascular device to a deployed state within the patient's vessel;

performing the medical procedure, the vascular device trapping emboli or thrombus;

translating the handle proximally relative to the fluid port section to retract the vascular device to a contracted state within the lumen of the delivery sheath; and removing the vascular device and delivery sheath from the patient's vessel.

10. The method of claim 9 further comprising flushing the lumen of the delivery sheath with saline injected through a side port of the fluid port section.

11. The method of claim 10 further comprising drawing suction through the side port to remove blood from an operative site at a distal end of the delivery sheath.

12. The method of claim 10 further comprising delivering medicaments through the side port to an operative site at a distal end of the delivery sheath.

13. The method of claim 8, wherein advancing the delivery catheter to a desired location within a patient's vessel further comprises rotating the handle with respect to the fluid port section to position a distal end of the elongated member within a desired branch of a bifurcated vessel.

14. Apparatus for deploying and retrieving a vascular device disposed on an elongated member from within a lumen of a delivery sheath, the apparatus comprising:

a handle configured to selectively grasp and release the elongated member; and a fluid port section coupled to the handle to allow translation and rotation therebetween, the fluid port section having a side port in fluid communication with the lumen of the delivery sheath and configured to allow the elongated member to pass therethrough to the handle.

15. The apparatus of claim 14, wherein the vascular device further comprises:

a support hoop attached to a distal region of the elongated member, the support hoop having an articulation region interposed between curved regions, and a blood permeable sac affixed to the support hoop so that the support hoop forms a mouth of the blood permeable sac.

16. The apparatus of claim 15, wherein the apparatus has a delivery state, wherein the handle is translated longitudinally to a proximal-most position relative to the fluid port section, and the support hoop is retracted within the delivery sheath, and a deployed state wherein the handle is translated longitudinally to a distal-most position adjacent the fluid port section, wherein the support hoop extends beyond a distal end of the delivery sheath and engages an interior wall of a patient's vessel.

17. The apparatus of claim 16, wherein the support hoop folds at the articulation region when the vascular device is contracted to the delivery state.

18. The apparatus of claim 16, wherein the mouth of the blood permeable sac is closed when the apparatus is in the delivery state.

19. The apparatus of claim 18 wherein opposite sides of the support hoop close towards one another when the apparatus is contracted to its delivery state.

20. The apparatus of claim 14 wherein the elongated member serves as a guide wire.

* * * * *